(12) United States Patent
Gindele et al.

(10) Patent No.: US 11,324,596 B2
(45) Date of Patent: *May 10, 2022

(54) INFLATABLE PENILE PROSTHESIS WITH REINFORCED CYLINDER

(71) Applicant: Boston Scientific Scimed, Inc., Maple Grove, MN (US)

(72) Inventors: Paul J. Gindele, Buffalo, MN (US); Matthew Lee Nelson, Plymouth, MN (US); Ryan Earl Fredrick, Eden Prairie, MN (US); Jonathan J. Lund, Glencoe, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 189 days.

This patent is subject to a terminal disclaimer.

(21) Appl. No.: 16/507,913

(22) Filed: Jul. 10, 2019

(65) Prior Publication Data

US 2020/0022813 A1 Jan. 23, 2020

Related U.S. Application Data

(60) Provisional application No. 62/700,643, filed on Jul. 19, 2018.

(51) Int. Cl.
*A61F 2/26* (2006.01)
(52) U.S. Cl.
CPC ........ *A61F 2/26* (2013.01); *A61F 2250/0013* (2013.01)

(58) Field of Classification Search
CPC .......................... A61F 2/26; A61F 2250/0013
See application file for complete search history.

(56) References Cited

U.S. PATENT DOCUMENTS

| 4,267,829 | A | 5/1981 | Burton et al. |
| 4,550,720 | A | 11/1985 | Trick et al. |
| 5,112,295 | A | 5/1992 | Zinner et al. |
| 6,558,315 | B1 * | 5/2003 | Kuyava .............. A61F 2/26 600/40 |
| 10,813,762 | B2 * | 10/2020 | Lund ................ A61F 2/26 |
| 2005/0014993 | A1 | 1/2005 | Mische et al. |

FOREIGN PATENT DOCUMENTS

| EP | 2992858 A1 | 3/2016 |
| WO | 2013096615 A1 | 6/2013 |

OTHER PUBLICATIONS

International Search Report and Written Opinion for Application No. PCT/US2019/041394, dated Oct. 18, 2019, 13 pages.

* cited by examiner

*Primary Examiner* — John P Lacyk
(74) *Attorney, Agent, or Firm* — Brake Hughes Bellermann LLP

(57) ABSTRACT

According to an aspect, an implant includes an inflatable member and a pump assembly configured to facilitate a transfer of a fluid from the reservoir to the inflatable member. The inflatable member defining a lumen and including a structural member. The inflatable member includes a coating.

20 Claims, 8 Drawing Sheets

INFLATABLE PENILE PROSTHESIS WITH REINFORCED CYLINDER

CROSS-REFERENCE TO RELATED APPLICATION

This application is a Nonprovisional of, and claims priority to, U.S. Patent Application No. 62/700,643, filed on Jul. 19, 2018, entitled "INFLATABLE PENILE PROSTHESIS WITH REINFORCED CYLINDER", which is incorporated by reference herein in its entirety.

TECHNICAL FIELD

This disclosure relates generally to bodily implants and more specifically to bodily implants, such as penile prostheses that include inflatable members.

BACKGROUND

One treatment for male erectile dysfunction is the implantation of a penile prosthesis that mechanically erects the penis. Some existing penile prostheses include inflatable cylinders or members that can be inflated or deflated using a pump mechanism. In some existing devices, the inflatable cylinder or member requires a relatively large amount of force to inflate. Additionally, in some existing devices, the pump mechanism may require many sequential squeezes or activations to inflate the cylinder or member.

Accordingly, it would be useful to provide a bodily implant, such as a penile prosthesis that includes an improved cylinder or member that can be more easily inflated.

SUMMARY

According to an aspect, an implant includes an inflatable member and a pump assembly configured to facilitate a transfer of a fluid from the reservoir to the inflatable member. The inflatable member defines a lumen and includes a structural member. The inflatable member includes a coating.

In some embodiments, at least a portion of the structural member is disposed within the lumen defined by the inflatable member.

In some embodiments, the coating is a molded coating. In some embodiments, the coating surrounds the lumen defined by the inflatable member. In some embodiments, the coating completely surrounds the lumen defined by the inflatable member.

In some embodiments, the structural member is flexible. In some embodiments, the structural member is a suture, a fiber, a filament or a membrane.

In some embodiments, the structural member is a first structural member, the inflatable member including a second structural member disposed within the lumen. In some embodiments, the structural member is a first structural member, the inflatable member including a second structural member disposed within the lumen, the first structural member being disposed substantially parallel to the second structural member.

In some embodiments, the inflatable member extends along a longitudinal axis, the structural member is a first structural member, the inflatable member including a second structural member disposed within the lumen, the first structural member is longitudinally spaced from the second structural member. In some embodiments, the structural member is a first structural member, the inflatable member including a second structural member and a third structural member, the second structural member being disposed within the lumen, the third structural member being disposed within the lumen.

In some embodiments, the device includes a reservoir configured to hold fluid, wherein the pump is configured to help facilitate a transfer of the fluid from the inflatable member to the reservoir when the implant is in a deflation mode.

In some embodiments, the pump assembly includes a valve housing and a pump bulb member.

In some embodiments, the coating includes a first molded portion and a second molded portion, the lumen defined by the elongate member is disposed between the first molded portion and the second molded portion. In some embodiments, the coating includes a first molded portion, a second molded portion, and a third molded portion.

In another implementation, a bodily implant includes an inflatable member, the inflatable member defining a lumen and including a structural member, at least a portion of the structural member being disposed within the lumen defined by the inflatable member, the inflatable member including a coating.

In some embodiments, the coating is a molded coating. In some embodiments, the coating includes a first molded portion and a second molded portion.

In yet another implementation, a method of making a bodily implant includes providing a member that includes a sidewall that defines a lumen; passing a structural member through the member at a first location of the member; and applying a coating to the member. In some embodiments, the method includes passing the structural member through the member at a second location of the member, the second location of the member being different than the first location of the member.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to medical devices such as penile prostheses or other bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human male, a human female, or any other mammal.

The embodiments discussed herein may improve the performance of an inflatable member of the device. For example, the inflatable member may have improved stiffness or rigidity, improved reliability, or improved deflation or inflation times. In some embodiments, the inflatable member may be facilitated by requiring less force or pressure to inflate the inflatable member.

The embodiments may include an inflatable penile prosthesis having a pump assembly, an inflatable member, and a reservoir. The inflatable member may be implanted into the corpus cavernosae of a patient or user, the reservoir may be implanted in the user's abdomen, and the pump assembly may be implanted in the scrotum. The pump assembly may switch between an inflation position and a deflation position such that a user can operate the device to place the inflatable penile prosthesis in either an inflation mode to transfer fluid from the reservoir to the inflatable member or a deflation mode to transfer the fluid from the inflatable member back to the reservoir.

Figure 1:
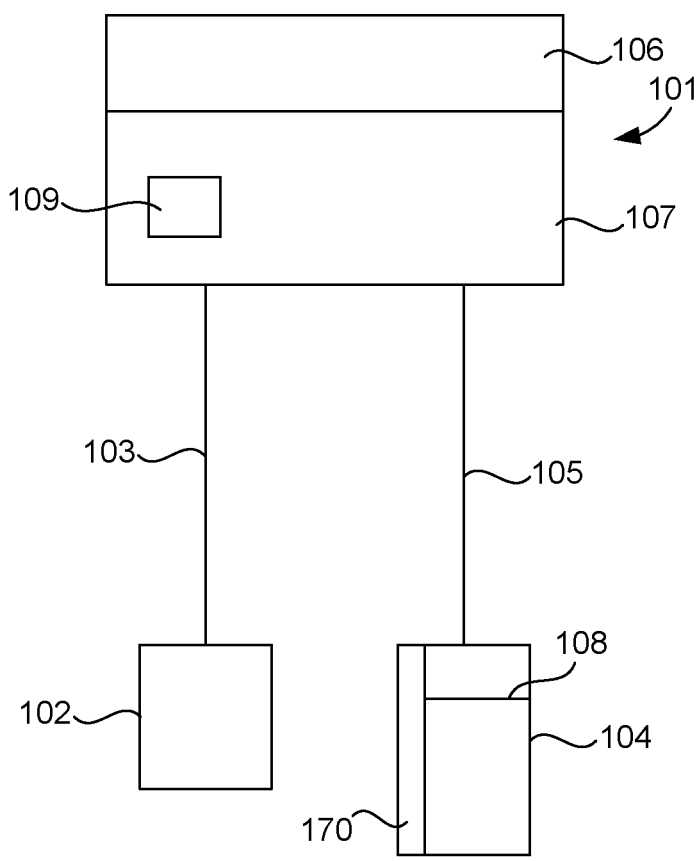
FIG. 1 schematically illustrates a penile prosthesis according to an embodiment.

FIG. 1 schematically illustrates an inflatable penile prosthesis 100 according to an aspect. The inflatable penile prosthesis 100 may include a reservoir 102, a cylinder or inflatable member 104, and a pump assembly 101 configured to transfer fluid between the reservoir 102 and the inflatable member 104. In some examples, the inflatable member 104 may be implanted into the corpus cavernosae of the user, the reservoir 102 may be implanted in the abdomen or pelvic cavity of the user (e.g., the reservoir 102 may be implanted in the lower portion of the user's abdominal cavity or the upper portion of the user's pelvic cavity), and the pump assembly 101 may be implanted in the scrotum of the user.

The inflatable member 104 may be capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of cylinders or at least two cylinders, e.g., a first cylinder member and a second cylinder member. The volumetric capacity of the inflatable member 104 may depend on the size of the cylinders. In some examples, the volume of fluid in each cylinder may vary from about 10 milliliters in smaller cylinders and to about 50 milliliters in larger sizes. In some examples, the first cylinder member may be larger than the second cylinder member. In other examples, the first cylinder member may have the same size as the second cylinder member.

In some embodiments, the inflatable member 104 includes a structural member 108. In some embodiments, the structural member 108 provides support to the inflatable member 104. For example, the structural member 108 may provide support to the inflatable member 104 when the inflatable member is placed in its inflated configuration. In some embodiments, the structural member 108 may facilitate the inflation of the inflatable member 104. For example, the structural member 108 may allow the inflatable member to be inflated at a relatively low pressure. In some embodiments, this may allow the user to inflate the inflatable member 104 with less pumps or activations of the pump or may allow the user to apply less force to the pump to inflate the inflatable member 104. Details of the pump assembly 101 are described below.

In some embodiments, the structural member 108 is at least partially disposed within the cavity or lumen of the inflatable member 104. For example, in some embodiments, the structural member 108 may extend from one portion of the inflatable member 104 to another portion of the inflatable member 104.

In some embodiments, the inflatable member 104 includes more than one structural member 108. For example, the inflatable member 104 may include two, three, four, or many structural members. In some embodiments, the structural members 108 are disposed apart from each other and extend along a length or longitudinal axis of the inflatable member 104. In some embodiments, one of the structural members is disposed offset or at an angle with respect to another of the structural members. In other embodiments, one of the structural members is disposed parallel to or substantially parallel to another of the structural members.

In some embodiments, the structural member 108 is flexible. In some embodiments, the structural member 108 is formed of a suture or other filament. In other embodiments, the structural member 108 is formed of another material. In some embodiments, the structural member 108 is formed of an elastic material. In other embodiments, the structural member 108 is formed of a non-elastic material.

In some embodiments, the inflatable member 104 includes a coating 170. In some embodiments, the coating 170 forms an outer surface or outer layer of the inflatable member 104. In some embodiments, the coating 170 extends around an entire outer surface of the inflatable member 104. In other embodiments, the coating 170 extends around or forms only a portion of the outer surface.

In some embodiments, the coating 170 is formed of an overmolded or extruded polymer. In other embodiments, the coating 170 is formed of another material, such as another biocompatible material.

The reservoir 102 may include a container having an internal chamber configured to hold or house fluid that is used to inflate the inflatable member 104. The volumetric capacity of the reservoir 102 may vary depending on the size of the inflatable penile prosthesis 100. In some examples, the volumetric capacity of the reservoir 102 may be 3 to 150 cubic centimeters. In some examples, the reservoir 102 is constructed from the same material as the inflatable member 104. In other examples, the reservoir 102 is constructed from a different material than the inflatable member 104.

The inflatable penile prosthesis 100 may include a first conduit connector 103 and a second conduit connector 105. Each of the first conduit connector 103 and the second conduit connector 105 may define a lumen configured to transfer the fluid to and from the pump assembly 101. The first conduit connector 103 may be coupled to the pump assembly 101 and the reservoir 102 such that fluid can be transferred between the pump assembly 101 and the reservoir 102 via the first conduit connector 103. For example, the first conduit connector 103 may define a first lumen configured to transfer fluid between the pump assembly 101 and the reservoir 102. The first conduit connector 103 may include a single or multiple tube members for transferring the fluid between the pump assembly 101 and the reservoir 102.

The second conduit connector 105 may be coupled to the pump assembly 101 and the inflatable member 104 such that fluid can be transferred between the pump assembly 101 and the inflatable member 104 via the second conduit connector 105. For example, the second conduit connector 105 may define a second lumen configured to transfer fluid between the pump assembly 101 and the inflatable member 104. The second conduit connector 105 may include a single or multiple tube members for transferring the fluid between the pump assembly 101 and the inflatable member 104. In some examples, the first conduit connector 103 and the second conduit connector 105 may include a silicone rubber material.

The pump assembly 101 may switch between an inflation mode in which the fluid in the reservoir 102 is transferred to the inflatable member 104 through the pump assembly 101 in a first direction (e.g., inflation direction) and a deflation mode in which the fluid in the inflatable member 104 is transferred back to the reservoir 102 through the pump assembly 101 in a second direction (e.g., deflation direction).

The pump assembly 101 includes a pump (also referred to as a pump bulb member) 106 and a valve body 107. The valve body 107 also includes a selection member 109. The selection member 109 may be used to select or change the mode in which the pump assembly is in. For example, the selection member 109 may be moved from a first position to a second position to place the device in its deflation mode. The selection member 109 may then be moved back to its first position to place the device in its inflation mode. In some embodiments, the selection member 109 is movable with respect to the valve body 107. For example, in some embodiments, the selection member 109 is slidably coupled or slideable with respect to the valve body 107.

The pump 106 may be squeezed or depressed by the user in order to facilitate the transfer of fluid from the reservoir 102 to the inflatable member 104. For example, in the inflation mode, while the user is operating the pump 106, the pump 106 may receive the fluid from the reservoir 102, and then output the fluid to the inflatable member 104. When the user switches to the deflation mode, at least some of the fluid can automatically be transferred back to the reservoir 102 (due to the difference in pressure from the inflatable member 104 to the reservoir 102). Then, the user may squeeze the inflatable member 104 to facilitate the further transfer of fluid through the pump 106 to the reservoir 102.

In some examples, the pump 106 may include a flexible member defining a cavity. In some examples, the pump 106 may define a pump shell having a flexible bulb and a valve body connector, where the valve body connector is designed to fit at least partially over the valve body 107. In some examples, the pump 106 may include a squeeze pump. In some examples, the pump 106 may include a portion that is round or substantially round. In some examples, the pump 106 may include ribbing or dimples to aid the user in gripping the pump 106. The pump 106 may use suction and pressure to move the fluid in and out of the cavity of the pump 106 in the inflation mode. For example, the user may depress or squeeze the pump 106 to expel the fluid out of the cavity, and, when the flexible member returns to its original shape, the resulting suction pushes the fluid into the cavity of the pump 106. In some examples, the pump 106 may have a bulb spring rate that is designed to refill the pump 106 in a selected time frame.

As discussed above, the selection member 109 may be used to select or change the mode in which the pump assembly is in. For example, in one embodiment, the selection member 109 may be placed in the inflate position and the user may then operate the pump 106 to inflate the inflatable member 104 (i.e., move the fluid from the reservoir 102 to the inflatable member 104). For example, the user may repeatedly depress or squeeze the pump 106 until the desired rigidity is achieved.

In some examples, if the reservoir 102 is at least partially pressurized, the fluid may automatically flow out of the reservoir 102 and into the inflatable member 104 without the user depressing or squeezing the pump 106 until the pressure is at least partially equalized between the reservoir 102 and the inflatable member 104.

Then, when the user wants to deflate the inflatable member 104, the user moves selection member 109 to its deflated position. The user may then operate the pump 106 to deflate the inflatable member 104 (i.e., move the fluid from the inflatable member 104 to the reservoir 102). The pump 106 may then return to its original form, which provides a suction force causing fluid to be drawn into the pump 106 from the inflation member 104. The fluid from the inflation member 104 fills the pump 106 (or at least partially fills the pump 106). This pump cycle is repeated until the inflatable member 104 is deflated.

In some examples, the fluid may automatically (upon movement of the selection member 109 to its deflate position) flow out of the inflatable member 104 and into the reservoir 102 without the user depressing or squeezing the pump 106 until the pressure is at least partially equalized between the reservoir 102 and the inflatable member 104.

In some examples, after the inflation member 104 has been deflated, the pump 106 may be squeezed to place the pump in a contracted position or configuration.

Figure 2:
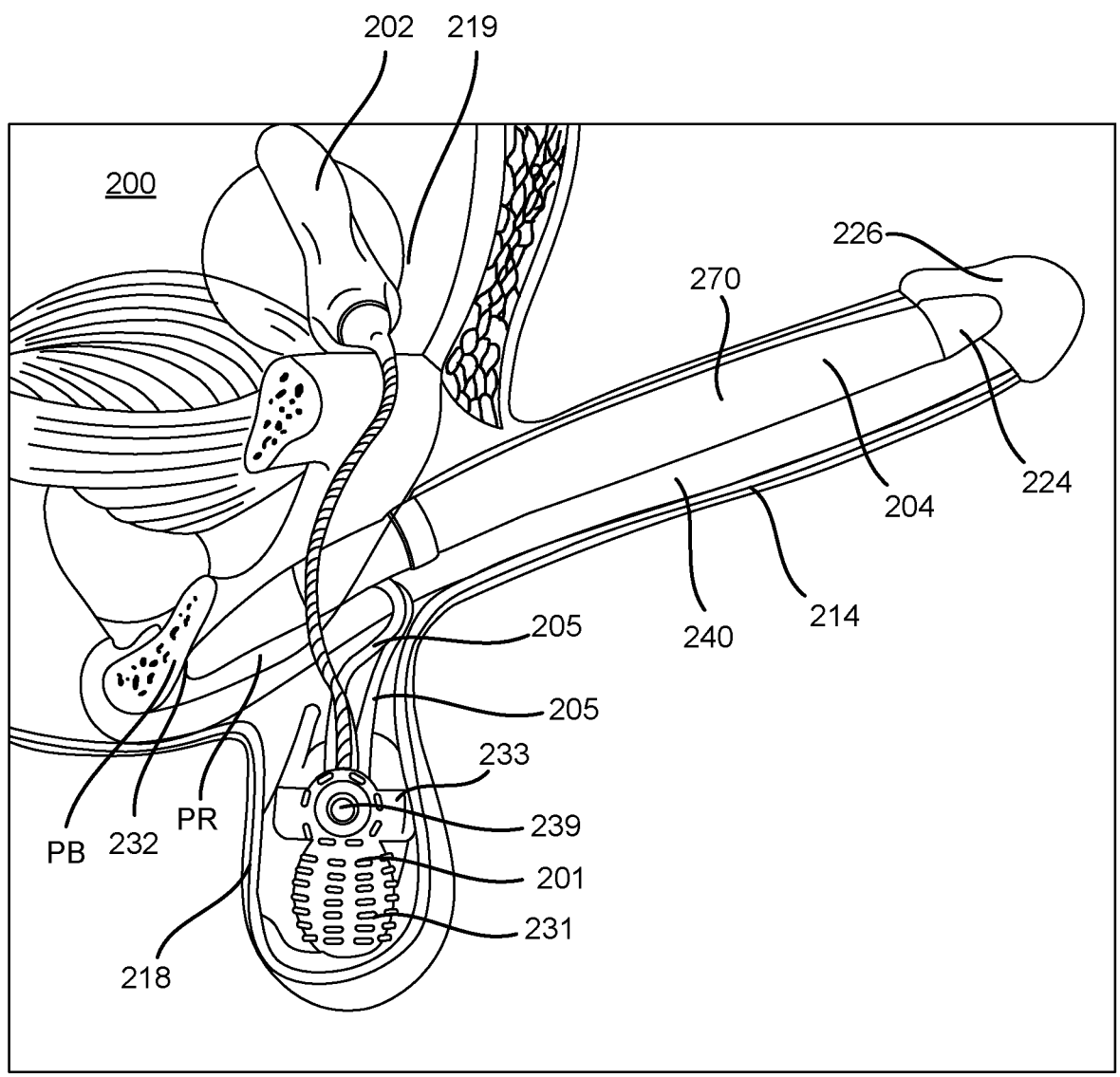
FIG. 2 illustrates a penile prosthesis implanted within a patient according to an embodiment.
Figure 3:
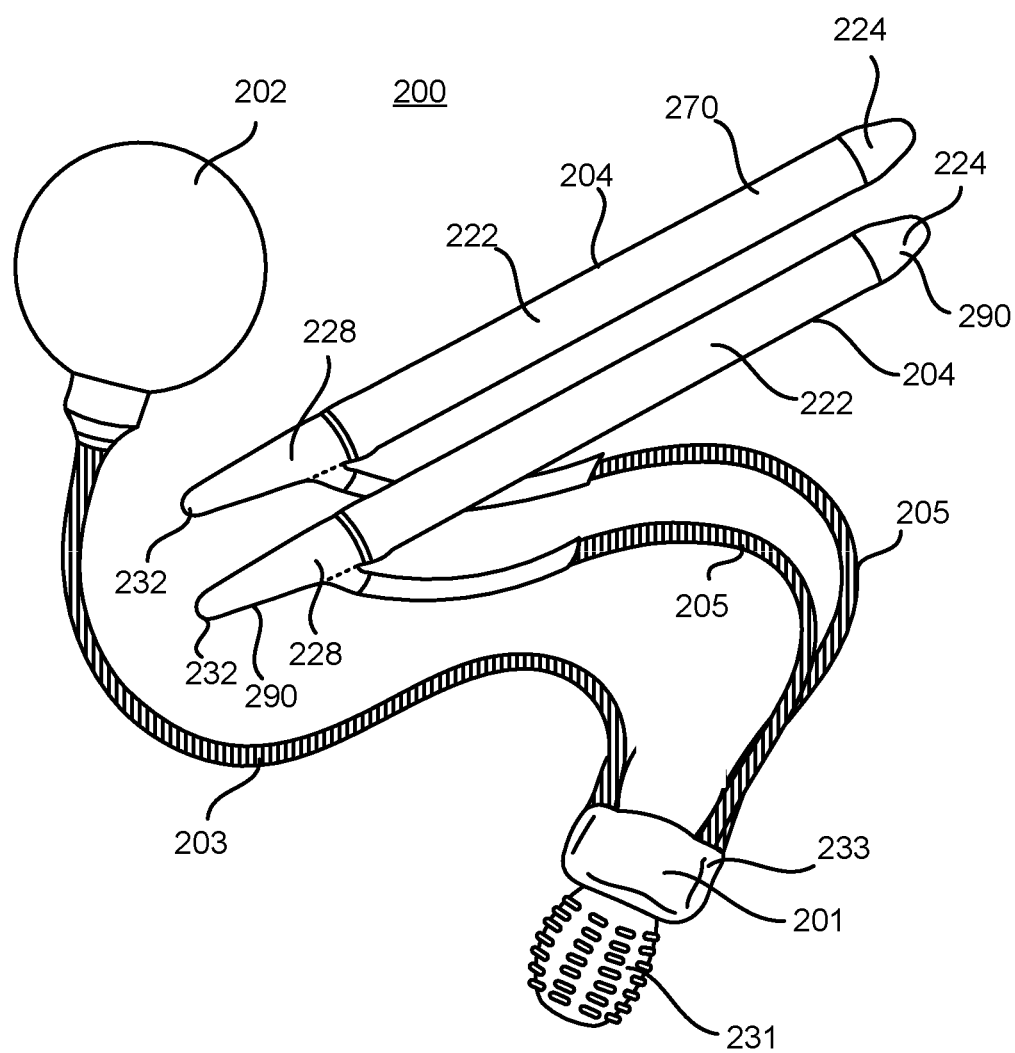
FIG. 3 is a perspective view of the penile prosthesis of FIG. 2.
Figure 4:
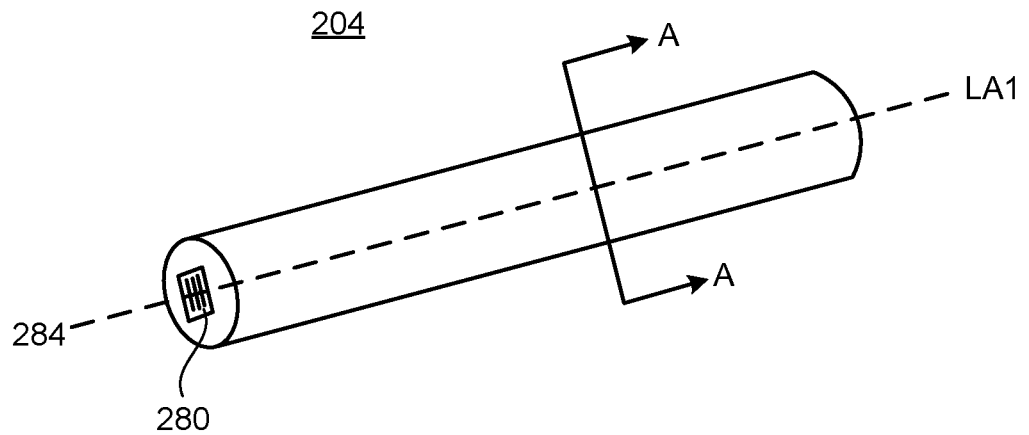
FIG. 4 is a perspective view of an inflatable member of the penile prosthesis of FIG. 2.
Figure 5:
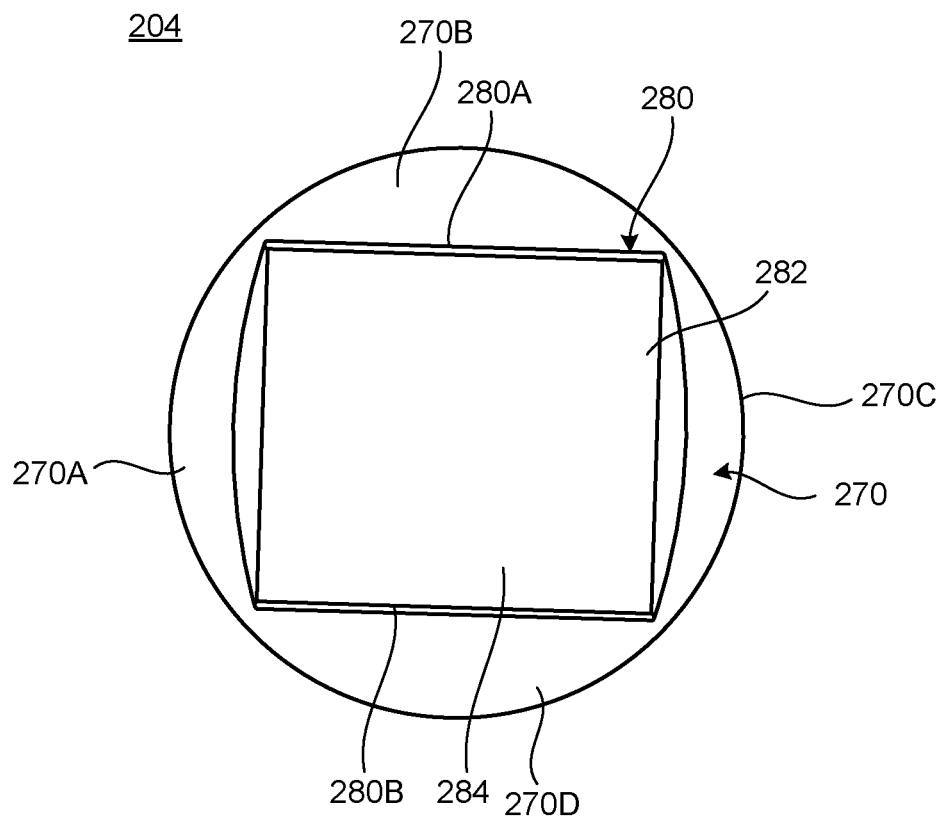
FIG. 5 is a cross-sectional view of the inflatable member of FIG. 4 taken along line A-A of FIG. 4.

FIG. 2 illustrates a penile prosthesis 200 implanted within a user according to an aspect. FIG. 3 is a perspective view of the penile prosthesis 200. FIGS. 4 and 5 illustrate portions of an inflatable member of the penile prosthesis.

The penile prosthesis 200 may include a pair of cylinders 204, and the pair of cylinders or inflatable members 204 are implanted in a penis 214. For example, one of the cylinders 204 may be disposed on one side of the penis 214. The other cylinder 204 (not shown in FIG. 2) of the pair of cylinders may be disposed on the other side of the penis 214. The cylinder 204 may include a distal end portion 224, a cavity or inflation chamber 222, and a proximal end portion 228 having a rear tip 232.

The penile prosthesis 200 may include a pump assembly 201, which may be implanted into the patient's scrotum 218. A pair of conduit connectors 205 may attach the pump assembly 201 to the pair of inflatable members or cylinders 204 such that the pump assembly 201 is in fluid communication with the pair of inflatable members or cylinders 204. Also, the pump assembly 201 may be in fluid communication with a reservoir 202 via a conduit connector 203. The reservoir 202 may be implanted into the user's abdomen 219. The inflation chamber or portion 222 of the cylinder 204 may be disposed within the penis 214. The distal end portion 224 of the cylinder 204 may be at least partially disposed within the crown portion 226 of the penis 214. The proximal end portion 228 may be implanted into the patient's pubic region PR with the rear tip 232 proximate the pubic bone PB.

In order to implant the inflatable members or cylinders 204, the surgeon first prepares the patient. The surgeon often makes an incision in the penoscrotal region, e.g., where the base of the penis 214 meets with the top of the scrotum 218. From the penoscrotal incision, the surgeon may dilate the patient's corpus cavernosae 240 to prepare the patient to receive the pair of inflatable members or cylinders 204. The corpus cavernosum is one of two parallel columns of erectile tissue forming the dorsal part of the body of the penis 214, e.g., two slender columns that extend substantially the length of the penis 214. The surgeon will also dilate two regions of the pubic area (proximal corpora cavernosae) to prepare the patient to receive the proximal end portion 228. The surgeon may measure the length of the proximal and distal corpora cavernosae from the incision and the dilated region of the pubic area to determine an appropriate size of the inflatable members or cylinders 204 to implant.

After the patient is prepared, the penile prosthesis 200 is implanted into the patient. The distal tip of the distal end portion 224 of each cylinder 204 may be attached to a suture. The other end of the suture may be attached to a needle member (e.g., Keith needle). The needle member is inserted into the incision and into the dilated corpus cavernosum. The needle member is then forced through the crown of the penis 214. The surgeon tugs on the suture to pull the cylinder 204 into the corpus cavernosum. This is done for each cylinder of the pair of cylinders 204. Once the inflation chamber 222 is in place, the surgeon may remove the suture from the distal tip. The surgeon then inserts the proximal end portion 228. The surgeon inserts the rear end of the cylinder 204 into the incision and forces the proximal end portion 228 toward the pubic bone PB until each cylinder 204 is in place.

In the illustrated embodiment, each of the inflatable members or cylinders 204 is structurally and functionally similar. Accordingly, only one of the inflatable members or cylinders will be discussed in detail. The inflatable member 204 may be capable of expanding upon the injection of fluid into a cavity of the inflatable member 204. For instance, upon injection of the fluid into the inflatable member 204, the inflatable member 204 may increase its length and/or width, as well as increase its rigidity. The volumetric capacity of the inflatable member 204 may depend on the size of the cylinders. In some examples, the volume of fluid in each cylinder may vary from about 10 milliliters in smaller cylinders and to about 50 milliliters in larger sizes.

In the illustrated embodiment, the inflatable member 204 includes a sidewall 280 that defines a lumen or cavity 282. The inflatable member 204 also includes a plurality of structural members 284. In some embodiments, the structural members 284 provide support to the inflatable member 204. For example, the structural members 284 may provide support to the inflatable member 204 when the inflatable member is placed in its inflated configuration. In some embodiments, the structural members 284 may facilitate the inflation of the inflatable member 204. For example, the structural members 284 may allow the inflatable member 204 to be inflated at a relatively low pressure. In some embodiments, this may allow the user to inflate the inflatable member 204 with less pumps or activations of the pump or may allow the user to apply less force to the pump to inflate the inflatable member 204. Details of the pump assembly 201 are described below.

In the illustrated embodiment, the structural members 284 are at least partially disposed within the cavity or lumen 282 of the inflatable member 204. For example, in some embodiments, the structural member 284 may extend from one portion of the inflatable member 204 to another, different portion of the inflatable member 204. Specifically, for example, one structural member may extend from a first portion of the sidewall 280A to a second, different portion of the sidewall 280B. In some embodiments, the structural member has a first portion that is coupled to the first portion of the sidewall 280A and a second portion that is coupled to the second portion of the sidewall 280B. In some embodiments, the structural members may extend through a center of the lumen 282. In other embodiments, the structural members extend adjacent to the center of the lumen 282.

The inflatable member 204 may include any number of structural members 284. In some embodiments, the structural members 284 may be different, separate members or pieces of material. In other embodiments, the structural members 284 may be a single unitary member that is passed through or coupled to the sidewall at various locations.

FIG. 5 is a cross-sectional view of the inflatable member 204 taken along line A-A of FIG. 4. In the illustrated embodiment, some of the structural members 284 are disposed or extend along axes that are parallel or substantially parallel to each other. For example, one structural member is disposed or extends parallel or substantially parallel to another structural member. In some embodiments, the structural members 284 are also disposed apart from each other along a length or longitudinal axis LA1 of the inflatable member 204.

In some embodiments, the structural member 284 is flexible. In the illustrated embodiment, the structural member 284 is formed of a suture or other filament. Specifically, in the illustrated embodiment, the more than one of the structural members is formed of a single suture or filament. In other embodiments, the structural member is formed of another material. In some embodiments, the structural member is formed of an elastic material. In other embodiments, the structural member is formed of a non-elastic material. In some embodiments, the structural member 284 is a fiber, a filament or a membrane. The structural member 284 may be formed of any type of material.

In the illustrated embodiment, the sidewall 280 is formed of a woven or fabric material. The structural member 284 is coupled to the sidewall at various locations by passing the structural member 284 though the fabric material. In some embodiments, the structural member 284 may be tied or otherwise coupled to the specific location or portion of the fabric material. In other embodiments, the sidewall is formed of another type of material.

In some embodiments, the inflatable member 204 is fluidically sealed. Accordingly, a fluid may be placed within the lumen 282 to inflate the inflatable member 204.

In the illustrated embodiment, the inflatable member 204 includes a coating 270. The coating 270 extends around or forms an outer surface of the inflatable member 204. In the illustrated embodiment, the coating 270 extends around or forms the entire outer surface of the inflatable member 204. In other embodiments, the coating 270 extends around or forms only a portion of the outer surface of the inflatable member 204.

In some embodiments, the coating 270 is formed of an overmolded or extruded elastic polymer. In other embodiments, the coating 270 is formed of another biocompatible material. In the illustrated embodiment, the coating 270 helps fluidically seal the inflatable member 204.

In the illustrated embodiment, the coating 270 includes four portions, 270A, 270B, 270C, and 270D. The portions of the coating 270 are arranged around the perimeter or outer surface of the inflatable member 204. In the illustrated embodiment, portion 270A is disposed opposite portion 270C (such that the cavity or lumen 282 is disposed between the portion 270A and the portion 270C. Similarly, portion 270B is disposed opposite portion 270D (such that the cavity or lumen 282 is disposed between the portion 270B and the portion 270D.

The pump assembly 201 may switch between an inflation mode in which the fluid in the reservoir 202 is transferred to the inflatable member 204 (or inflatable members) through the pump assembly 201 in a first direction (e.g., inflation direction) and a deflation mode in which the fluid in the inflatable member 204 (or inflatable members) is transferred back to the reservoir 202 through the pump assembly 201 in a second direction (e.g., deflation direction).

In some embodiments, an end caps or tips 224 and 232 are coupled to each of the end portions of the sidewall. In some embodiments, the end caps help facilitate the fluidic sealing of the lumen 282. The end caps may be coupled to the end portions of the sidewall via an adhesive or any other known coupling method. In some embodiments, the end caps may have different shapes.

The pump assembly 201 includes a pump bulb member or pump 231, a valve body 233, and a selection member 239. The selection member may be used to select or change the mode in which the pump assembly 201 is in. For example, the selection member 239 may be moved from a first position to a second position to place the device in its deflation mode. The selection member 239 may then be moved back to its first position to place the device in its inflation mode. In some embodiments, the selection member 239 is movable with respect to the valve body 233. For example, the selection member 239 may be slidably coupled or slideable with respect to the valve body 233. In some embodiments, the selection member 239 includes stop members, such as shoulders or detents that engage members of the valve body 233 to lock or help retain the selection member 239 in one of its first and second positions. In other embodiments, the selection member 239 may be disposed or coupled to another portion of the device.

The pump 231 may be squeezed or depressed by the user in order to facilitate the transfer of fluid from the reservoir 202 to the inflatable member 204. For example, in the inflation mode, while the user is operating the pump 231, the pump 231 may receive the fluid from the reservoir 202, and then output the fluid to the inflatable member 204. When the user switches to the deflation mode, at least some of the fluid can automatically be transferred back to the reservoir 202 (due to the difference in pressure from the inflatable member 204 to the reservoir 202). Then, the user may squeeze the inflatable member 204 to facilitate the further transfer of fluid through the pump 231 to the reservoir 202.

Then, when the user wants to deflate the inflatable members 204, the user moves selection member 239 to its deflate position. The user may then operate the pump 231 to deflate the inflatable members 204 (i.e., move the fluid from the inflatable members 204 to the reservoir 202). For example, the user may repeatedly depress or squeeze the pump 231 until the deflation is completed. The pump 231 may then return to its original form, which provides a suction force causing fluid to be drawn into the pump 231 from the inflation members 204. The fluid from the inflation members 204 fills the pump 231 (or at least partially fills the pump 231). This pump cycle is repeated until the inflatable members 204 are deflated.

In some examples, the fluid may automatically (upon movement of the selection member 239 to its deflate position) flow out of the inflatable member 204 and into the reservoir 202 without the user depressing or squeezing the pump 231 until the pressure is at least partially equalized between the reservoir 202 and the inflatable member 204.

In some examples, after the inflation member 204 has been deflated, the pump 231 may be squeezed to place the pump in a contracted position or configuration.

Figure 6:
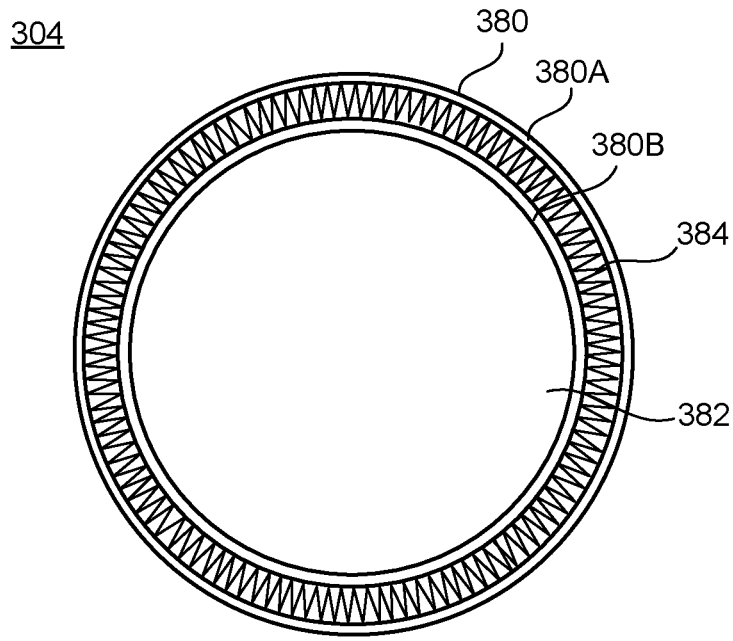
FIG. 6 is a cross-sectional view of an inflatable member of another embodiment.
Figure 7:
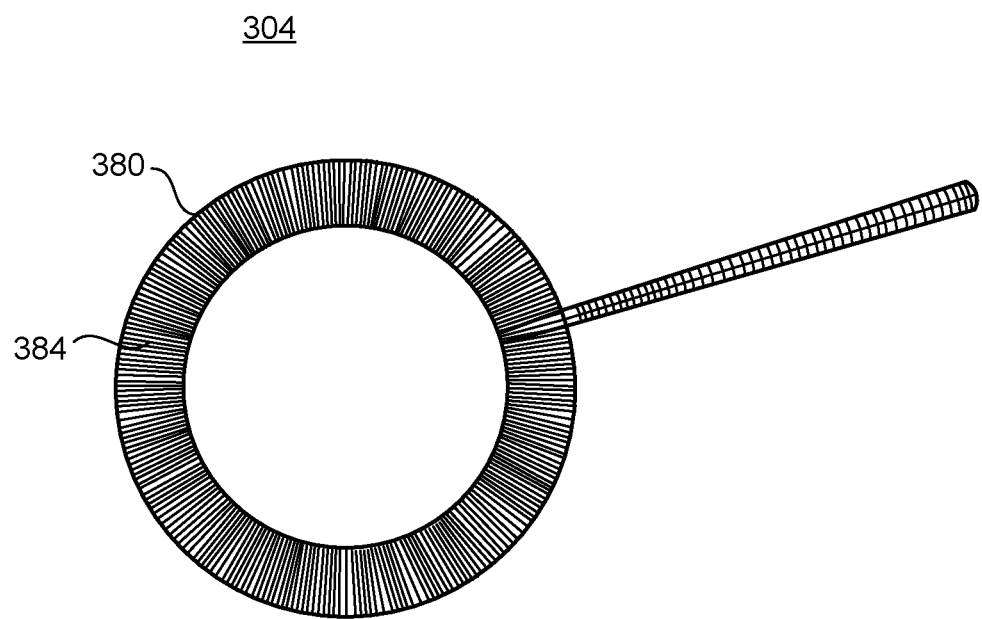
FIG. 7 is a perspective view of the inflatable member of FIG. 6.
Figure 8:
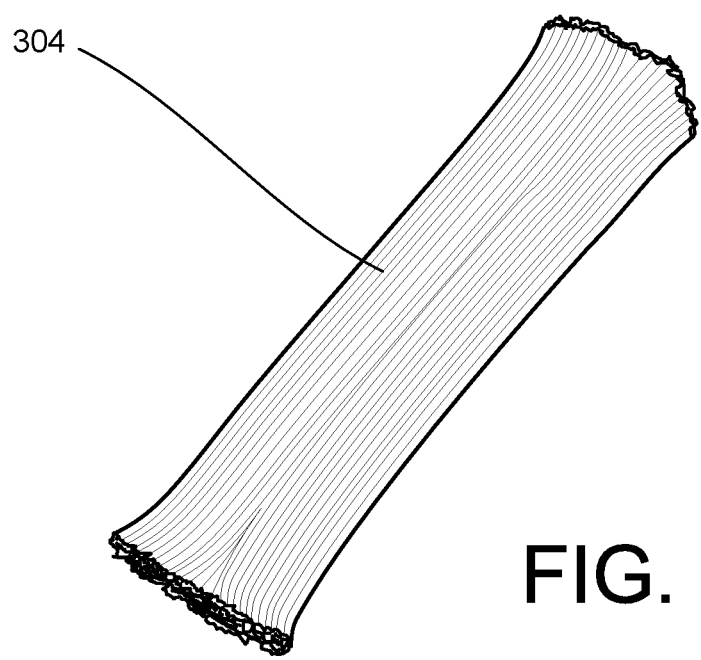
FIG. 8 is a top view of the inflatable member of FIG. 6.
Figure 9:
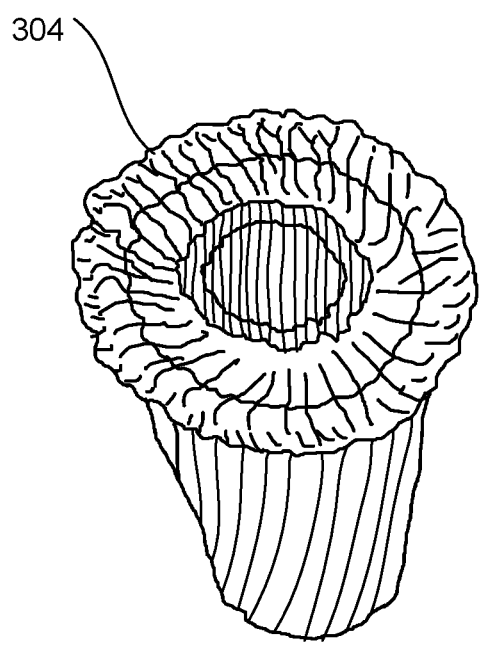
FIG. 9 is an end view of the inflatable member of FIG. 6.

FIG. 6 is a cross-sectional view of an inflatable member 304 according to an embodiment. FIG. 7 is a perspective view of the inflatable member 304. FIG. 8 is a top view of the inflatable member 304. FIG. 9 is an end view of the inflatable member 304. In the illustrated embodiment, the inflatable member 304 includes a sidewall 380 that defines a lumen or cavity 382. The sidewall 380 includes a first sidewall member or layer 380A and a second sidewall member or layer 380B. The inflatable member 304 also includes a plurality of structural members 384. In some embodiments, the structural members 384 provide support to the inflatable member 304. For example, the structural members 384 may provide support to the inflatable member 304 when the inflatable member is placed in its inflated configuration. In some embodiments, the structural members 384 may facilitate the inflation of the inflatable member 304. For example, the structural members 384 may allow the inflatable member 304 to be inflated at a relatively low pressure. In some embodiments, this may allow the user to inflate the inflatable member 304 with less pumps or activations of the pump or may allow the user to apply less force to the pump to inflate the inflatable member 304.

In the illustrated embodiment, the structural members 384 are at least partially disposed between the first sidewall member 380A and the second sidewall member 380B. The inflatable member 304 may include any number of structural members 384. In some embodiments, the structural members 384 may be different, separate members or pieces of material. In other embodiments, the structural members 384 may be a single unitary member that is passed through or coupled to the sidewall at various locations.

In some embodiments, the structural member 384 is flexible. In the illustrated embodiment, the structural member 384 is formed of a suture or other filament. Specifically, in the illustrated embodiment, the more than one of the structural members is formed of a single suture or filament. In other embodiments, the structural member is formed of another material. In some embodiments, the structural member is formed of an elastic material. In other embodiments, the structural member is formed of a non-elastic material. In some embodiments, the structural member 384 is a fiber, a filament or a membrane. The structural member 384 may be formed of any type of material.

In the illustrated embodiment, the sidewall 380 (for example, each sidewall member 380A and 380B) is formed of a woven or fabric material. The structural member 384 is coupled to the sidewall at various locations by passing the structural member 384 though the fabric material. In some embodiments, the structural member 384 may be tied or otherwise coupled to the specific location or portion of the fabric material. In other embodiments, the sidewall is formed of another type of material.

In some embodiments, the inflatable member 304 is fluidically sealed. Accordingly, a fluid may be placed within the lumen 382 to inflate the inflatable member 304. Specifically, in some embodiments, a fluid may be placed within the lumen 382 between the structural members to inflate the inflatable member 304.

In some embodiments, the inflatable member 304 includes a coating. The coating may extend around or form an outer surface of the outer sidewall layer 380A and may extend around or form an inner surface of the inner sidewall layer 380B.

In some embodiments, the coating is formed of an elastic polymer. In other embodiments, the coating is formed of another biocompatible material. In some embodiments, the coating helps fluidically seal the inflatable member 304.

As best illustrated in FIG. 7, the inflatable member 304 may be formed as a planar or sheet like member and then rolled to form the tubular shape. The ends of the planar or sheet like member may be coupled together, using for example, stitching, adhesive, or other coupling method. In some embodiments, one end of the planar or sheet like member is coupled directly to another end of the planar or sheet like member. In other embodiments, the end portions may be overlapped and then coupled together.

Figure 10:
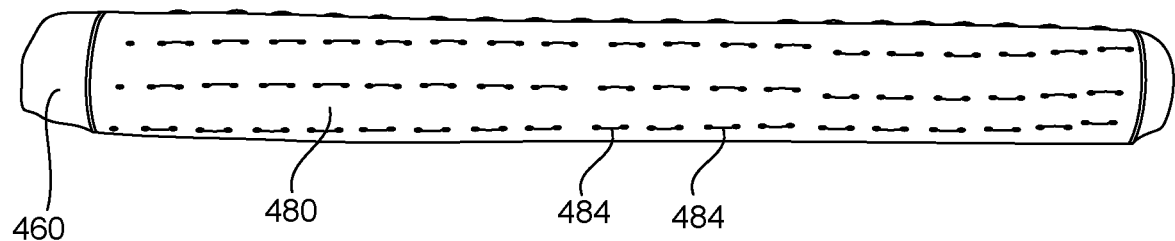
FIG. 10 is a top view of an inflatable member of another embodiment.
Figure 11:
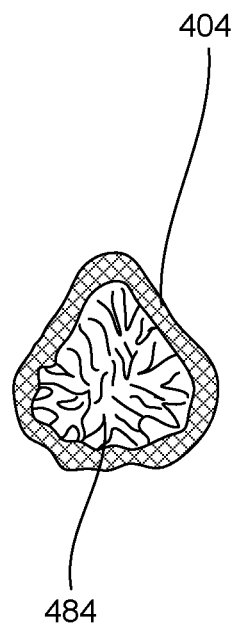
FIG. 11 is an end view of the inflatable member of FIG. 10.

FIGS. 10 and 11 illustrate an inflatable member 404 during a manufacturing process. In some embodiments, a rod or elongate member 460 is placed within the lumen defined by the sidewall 480. The rod or elongate member 460 may be configured to dissolve. For example, the rod or elongate member 460 may be water dissolvable. The rod may be sized and configured to slightly stretch or keep the sidewall in an expanded or uncollapsed form. The structural members 484 may then be coupled to the sidewall. For example, a filament that forms the structural member 484 may be passed through the inflatable member 404 and the rod or elongate member 460. Once the structural members 484 are in place the rod may be removed from the lumen. Specifically, in some embodiments, the rod may be dissolved (for example, by passing water through the lumen). FIG. 11 is an end view of the inflatable member 404 after the rod or elongate member 460 has been dissolved.

In some embodiments, the use of the rod or elongate member 460 during the manufacturing process may facilitate the placement of the structural members 484. For example, the rod or elongate member 460 may allow or facilitate the placement of uniform tension on the structural members 484. Additionally, the use of the rod or elongate member 460 may help prevent the formation of creases when the structural members 460 are placed.

Figure 12:
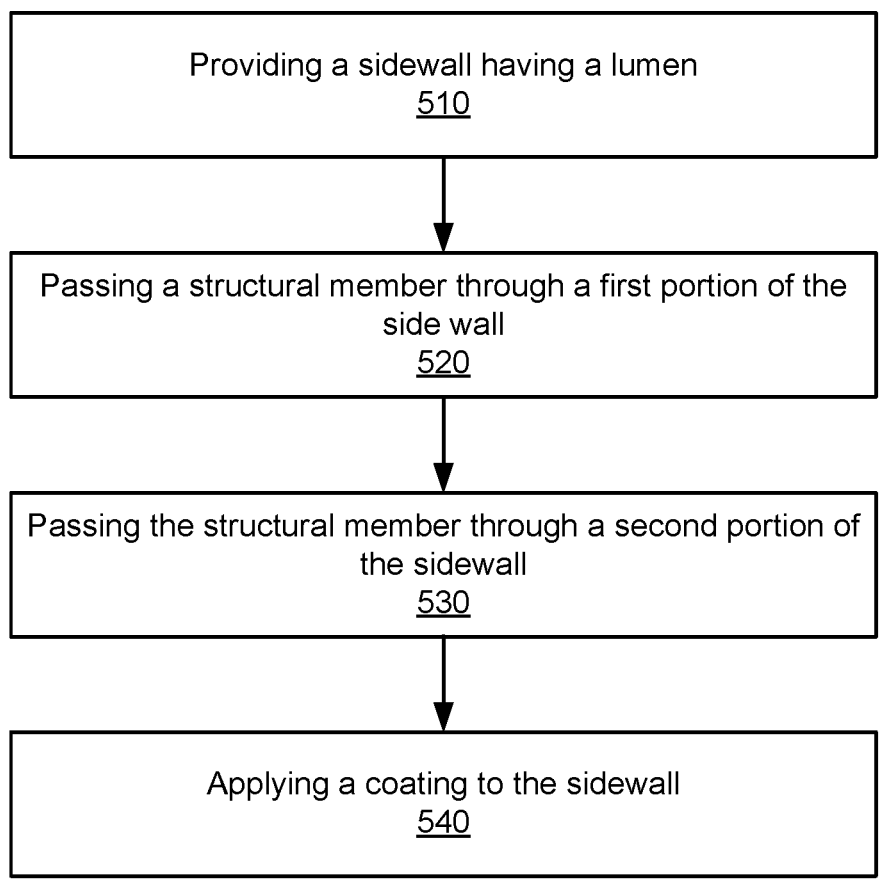
FIG. 12 is a flow chart of a method of making an inflatable member of a penile prosthesis according to an embodiment.

FIG. 12 is a flow chart for a method 500 of making or manufacturing an inflatable member according to an embodiment. At 510, a sidewall defining or having a lumen is provided. At 520, a structural member is passed through a portion of the sidewall at a first location. At 530, the structural member is passed through the sidewall at a second, different location. At 540, a coating is applied to the sidewall. In some embodiments, a rod or elongate member is placed or disposed within the lumen before the structural member is passed through a portion of the sidewall.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A penile implant, comprising:
    an inflatable member; and
    a pump assembly configured to facilitate a transfer of a fluid from a reservoir to the inflatable member,
    the inflatable member having a sidewall defining a lumen and including a structural member, the structural member passing through the sidewall, the inflatable member including a coating.

2. The penile implant of claim 1, wherein at least a portion of the structural member is disposed within the lumen defined by the inflatable member.

3. The penile implant of claim 1, wherein the coating is a molded coating.

4. The penile implant of claim 1, wherein the coating surrounds the lumen defined by the inflatable member.

5. The penile implant of claim 1, wherein the coating completely surrounds the lumen defined by the inflatable member.

6. The penile implant of claim 1, wherein the structural member is flexible.

7. The penile implant of claim 1, wherein the structural member is a suture, a fiber, a filament or a membrane.

8. The penile implant of claim 1, wherein the structural member is a first structural member, the inflatable member including a second structural member disposed within the lumen.

9. The penile implant of claim 1, wherein the structural member is a first structural member, the inflatable member including a second structural member disposed within the lumen, the first structural member being disposed substantially parallel to the second structural member.

10. The penile implant of claim 1, wherein the inflatable member extends along a longitudinal axis, the structural member is a first structural member, the inflatable member including a second structural member disposed within the lumen, the first structural member is longitudinally spaced from the second structural member.

11. The penile implant of claim 1, wherein the structural member is a first structural member, the inflatable member including a second structural member and a third structural member, the second structural member being disposed within the lumen, the third structural member being disposed within the lumen.

12. The penile implant of claim 1, further comprising:
    a reservoir configured to hold fluid,
    wherein the pump is configured to help facilitate a transfer of the fluid from the inflatable member to the reservoir when the implant is in a deflation mode.

13. The penile implant of claim 1, wherein the pump assembly includes a valve housing and a pump bulb member.

14. The penile implant of claim 1, wherein the coating includes a first molded portion and a second molded portion, the lumen defined by the elongate member is disposed between the first molded portion and the second molded portion.

15. The penile implant of claim 1, wherein the coating includes a first molded portion, a second molded portion, and a third molded portion.

16. A penile implant, comprising:
    an inflatable member, the inflatable member having a sidewall defining a lumen and including a structural member, the structural member extending through a portion of the sidewall, at least a portion of the structural member being disposed within the lumen defined by the sidewall, the inflatable member including a coating.

17. The penile implant of claim 16, wherein the coating is a molded coating.

18. The penile implant of claim 16, wherein the coating includes a first molded portion and a second molded portion.

19. A method of making an inflatable member of a penile implant, comprising:
   providing a member that includes a sidewall that defines a lumen;
   passing a structural member through the sidewall at a first location of the sidewall; and
   applying a coating to the member.

20. The method of claim 19, further comprising:
   passing the structural member through the sidewall at a second location of the sidewall, the second location of the sidewall being different than the first location of the sidewall.

* * * * *